Oct. 4, 1960 O. T. BOLDING, SR Plant Pat. 1,974
APPLE TREE
Filed Dec. 29, 1959
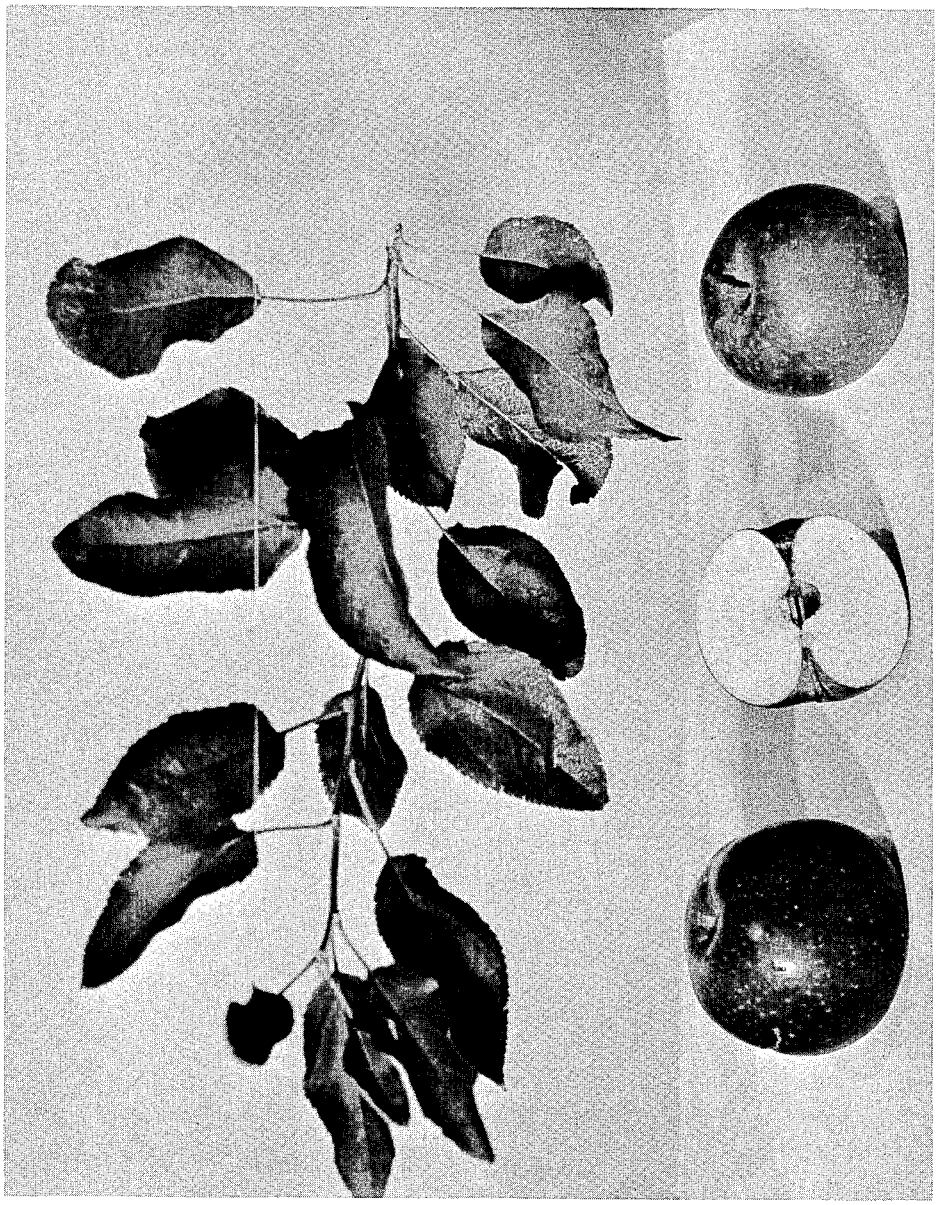
INVENTOR
Oron T. Bolding Sr.
BY Robb & Robb
ATTORNEYS United States Patent Office Plant Pat. 1,974
Patented Oct. 4, 1960

1,974

APPLE TREE

Oron T. Bolding, Sr., Sylacauga, Ala.

Filed Dec. 29, 1959, Ser. No. 862,718

1 Claim. (Cl. 47—62)

The present invention relates to a new and distinct variety of apple tree which was originated by me from seed which I planted on my property near Sylacauga, Alabama, and which I obtained from a small yellow summer apple of unknown origin and identity.

For many years, I have spent considerable time in working with fruit trees in an effort to develop new and improved varieties. Much of this time has been devoted to experimentation with seedlings grown from seeds planted by me as acquired from various sources. The present new seedling originated from this experimental program, and after a prolonged period of observation thereof, has fully proven itself to be endowed with unusual and superior characteristics which definitely differentiate the same from all other apple varieties of which I am aware, as evidenced by the following characteristics which are outstanding in the new variety and represent a unique and comercially desirable combination:

(1) A vigorous and upright habit of growth (more vigorous and more upright than "Winesap" apples);

(2) Late-blooming and fruit-ripening habits, with the fruit ripening in the area of Sylacauga, Alabama, about November 10 to 15, which is later than the ripening of any other good dessert apple known in the South;

(3) Regular and very productive bearing habits;

(4) Unusually large size of the fruit (each averaging about 1½ pounds and over 4 inches in transverse diameter at the time of picking);

(5) Good flavor, comparable to that of the variety commercially distributed under the registered trademark "Delicious" (unpatented); and (6) Good resistance to both hot weather and the usual other troubles and diseases normally encountered in southern apple growing.

Asexual reproduction of my new apple variety, as performed by budding at Sylacauga, Alabama, and by bench grafting at Baileyton, Alabama, shows that the foregoing characteristics and distinctions come true to form and are established and transmitted through succeeding propagations.

The accompanying drawing shows typical specimens of the foilage and fruit of my new variety, including both exterior and sectional views of fruit specimens.

The following is a detailed description of my new variety, as based upon observations of specimens grown at Sylacauga, Alabama, and Auburn, Alabama, with color terminology in accordance with Nickerson's Color Fan, published by Munsell Color Company, Inc., of Baltimore, Maryland, except where general color terms of ordinary dictionary significance are obvious:

Dates first and last picking: About October 15 and about November 17, respectively.

Tree: Medium size; vigorous; upright; tall; open-topped; rapid growing; hardy; very productive; regular bearer.

*Trunk.*—Medium stockiness; smooth.

*Branches.*—Medium thickness; smooth; little-branching. Color of bark—Brownish Grey, Color No. 10 YR 3/1. Lenticels—numerous; large.

*Leaves.*—Large; wide; long; ovate; abruptly pointed; thick; smooth. Color—Moderate Olive Green, Color No. 7.5 GY 4/4. Length—from 4 inches to 5 inches. Width—from 2 inches to 3 inches. Margins—coarsely serrate. Petiole—long (from 1½ inches to 2 inches); thick.

Flowers: Late as compared with other varieties (about April 1 through April 10); large size.

*Color.*—Pale Pink, Color No. 2.5 R 9/3.

*Quantity.*—Very profuse.

Fruit: Maturity when described—ripe.

*Harvest date.*—About November 10 to about November 15.

*Size.*—Large. Axial diameter—3¾ inches on average. Transverse diameter—4¼ inches on average.

*Form.*—Oblique; oblate.

*Cavity.*—Unsymmetrical; rounded; acuminate; undulate; pubescent. Depth—⅞ inch. Breadth—1 inch x ¾ inch. Markings—none.

*Basin.* — Symmetrical; rounded; wide base; undulate; pubescent. Depth—from ⅜ inch to 7/16 inch. Breadth—1 inch. Markings—none.

*Stem.* — Clubbed; medium stoutness; pubescent. Length—1 inch. Breadth—1/16 inch. Markings—none.

*Calyx.*—Open; segments persistent; lanceolate; obtuse. Length—¼ inch. Outer surface—pubescent. Inner surface—pubsecent.

*Eye.*—Medium size; open.

*Skin.*—Tender; semi-glossy; waxed. Dots—conspicuous; large; even; from oblong to circular; color—white; distribution—close together near basin. Ground color (where leaves prevent development of blush)—Brilliant Yellow, Color No. 2.5 Y 9/9. Color markings—blushed; bright; self-colored to solid red. Bloom—moderate; distribution — uniform; scarfskin — wanting. General color effect (blush)—Dark Red, Color No. 5 R 3/7.

*Flesh.*—Juicy. Color—from Yellow, Color No. 7.5 to white. Texture—firm; crisp; melting. Flavor—mild; rich. Aroma—Distinct. Total soluble solids (approximate amount of sugar)—16.3%. Quality—from good to best.

*Core.*—Median. Alternate bundle—reaches tube below stamens. Core lines—meeting; distinct in cross-section. Carpellary area—indistinct; large. Calyx tube—pubescent; cone shape; long funnel stem; depth of tube to shoulder ½ inch; entire depth 1⅛ inches. Styles—pubescent. Stamens—distinct; basal. Axillary cavity—present. Seed cells—abaxile; open; cell walls: length—¾ inch; breadth—¼ inch; longitudinal section—mucronate.

Seeds:

*Number.*—5 perfect and 2 imperfect. Largest number in one cell—2.

*Length.*—5/16 inch.

*Breadth.*—3/16 inch.

*Form.*—Obtuse.

*Color.*—Moderate Reddish Brown, Color No. 10 R 3/4.

Insect and disease resistance: Has shown no evidence of susceptibility to either disease or insects over prolonged period of observations in Alabama area, and while given normal care by spraying regularly in the spring, summer and dormant stages.

Use: Dessert.

Keeping Quality: Good. Number of days in ordinary storage—about 90 days at ordinary temperature, without refrigeration.

I claim:

A new and distinct variety of apple tree, substantially as herein shown and described, characterized particularly as to novelty by the unique combination of a vigorous and upright habit of growth, late-blooming and fruit-ripening habits, regular and very productive fruit-bearing habits, unusually large size of the fruit, good flavor and good keeping qualities thereof, and good resistance to hot weather, diseases and other troubles commonly encountered in the growing of apples in the Southern areas of the United States.

No references cited.